US00PP20229P2

(12) United States Plant Patent
Pedersen

(10) Patent No.: US PP20,229 P2
(45) Date of Patent: Aug. 25, 2009

(54) ***LAVANDULA* PLANT NAMED 'SILVER SUMMER'**

(50) Latin Name: *Lavandula stoechas*
Varietal Denomination: Silver Summer

(75) Inventor: Jens Ingemann Pedersen, Odense N (DK)

(73) Assignee: Gartneriet Tvillinge Gaarden A/S, Odense N (DK)

( * ) Notice: Subject to any disclaimer, the term of this patent is extended or adjusted under 35 U.S.C. 154(b) by 0 days.

(21) Appl. No.: 12/214,190

(22) Filed: Jun. 17, 2008

(51) Int. Cl.
*A01H 5/00* (2006.01)

(52) U.S. Cl. ..... Plt./445

(58) Field of Classification Search ..... Plt./445
See application file for complete search history.

*Primary Examiner*—Annette H Para
(74) *Attorney, Agent, or Firm*—Jondle & Associates, P.C.

(57) ABSTRACT

A *Lavandula* cultivar particularly distinguished by foliage that has a strong intensity of grey and a low intensity of green, a globular plant shape with low to moderate vigor and violet-blue flowers on a tall spike is disclosed.

2 Drawing Sheets

Genus and species: *Lavandula stoechas.*
Variety denomination: 'Silver Summer'.

BACKGROUND OF THE NEW PLANT

The present invention comprises a new and distinct cultivar of *Lavandula,* botanically known as *Lavandula stoechas,* and hereinafter referred to by the cultivar name 'Silver Summer'. The new cultivar originated from a naturally occurring whole plant mutation of the *Lavandula stoechas* parent 'Alexandra' (unpatented).

The new cultivar was discovered in July 2006 in Komen, Belgium, and has been asexually reproduced repeatedly by vegetative cuttings in Komen, Belgium and Mijdrecht, The Netherlands over a two-year period. The present invention has been found to retain its distinctive characteristics through successive asexual propagations.

Plant Breeder's Rights for this cultivar have been applied for in Europe on Aug. 1, 2007. 'Silver Summer' has not been made publicly available more than one year prior to filing of this application.

SUMMARY OF THE INVENTION

The following are the most outstanding and distinguishing characteristics of the new cultivar when grown under normal horticultural practices in Komen, Belgium and Mijdrecht, The Netherlands.

1. Foliage that has a strong intensity of grey and a low intensity of green;
2. A globular plant shape with low to moderate vigor; and
3. Violet-blue flowers on a tall spike.

DESCRIPTION OF THE PHOTOGRAPHS

This new *Lavandula* plant is illustrated by the accompanying photographs which show overall plant habit including inflorescences, buds, and foliage of the plant; the colors shown are as true as can be reasonably obtained by conventional photographic procedures. The photos are of a 3-year-old plant grown in a 1.5 liter container in Mijdrecht, The Netherlands in May 2008.

DESCRIPTION OF THE NEW CULTIVAR

Figure 1:
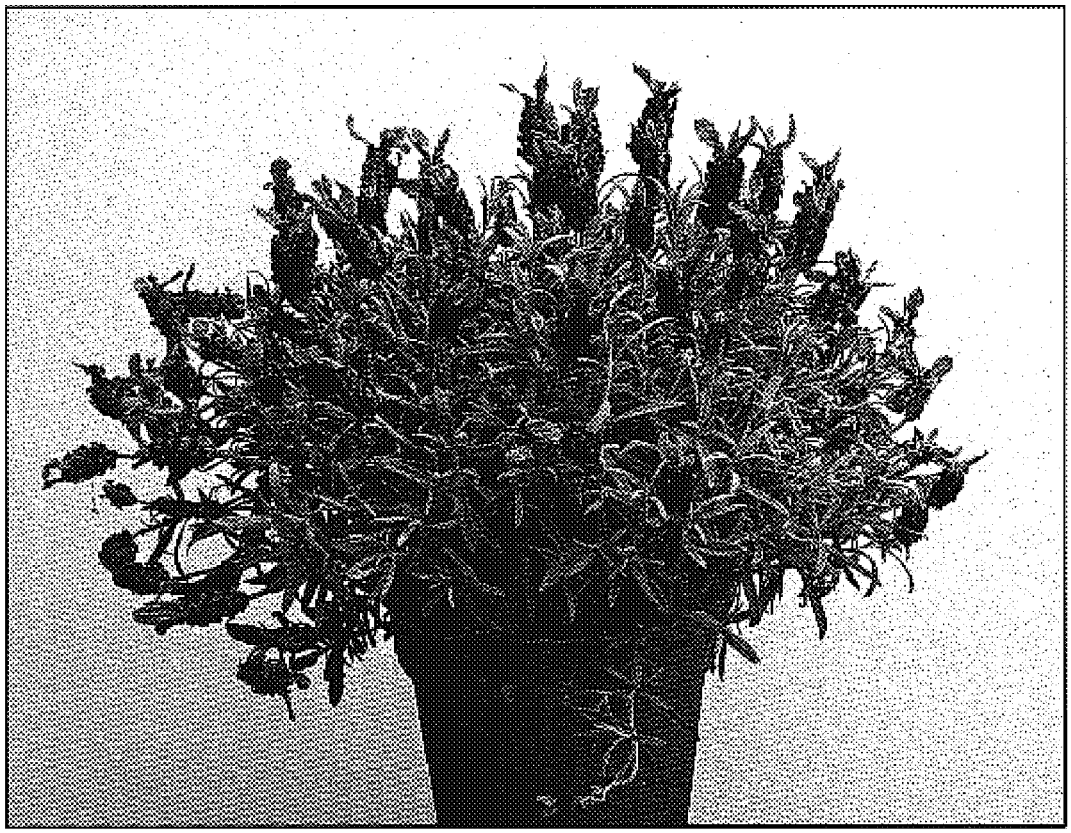
FIG. 1 shows the overall plant habit including inflorescences and foliage.
Figure 2:
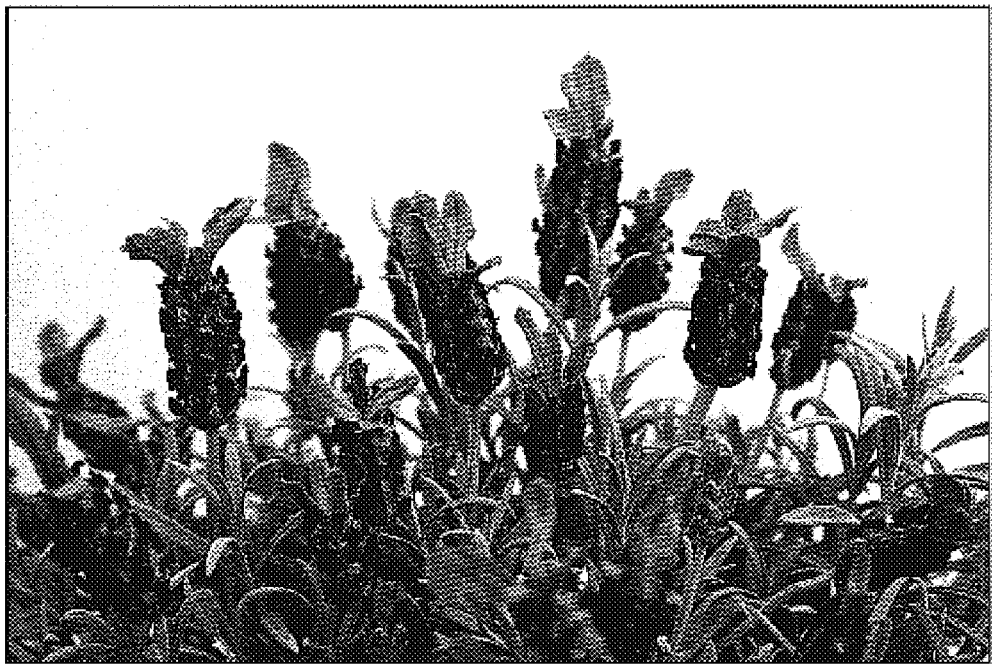
FIG. 2 shows a close-up view of the inflorescences.
Figure 3:
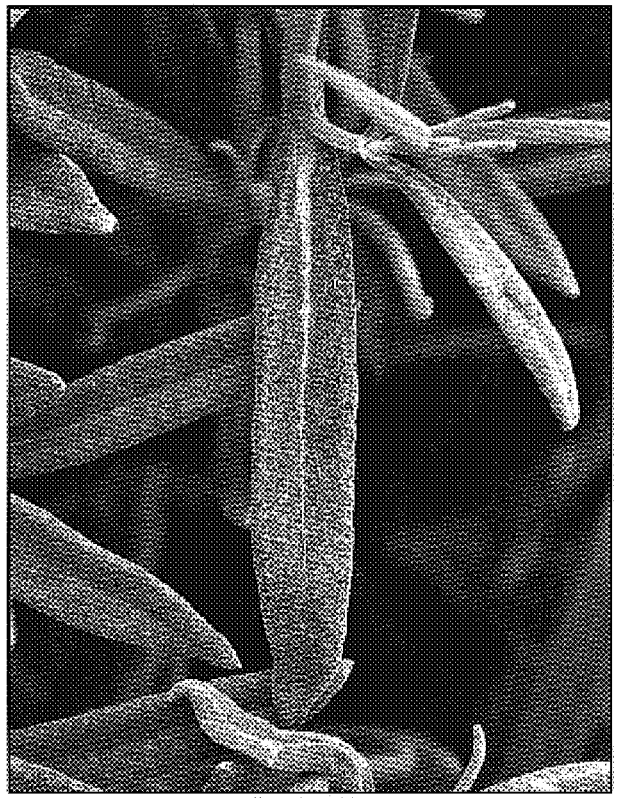
FIG. 3 shows a close-up view of the mature leaves.

The following detailed descriptions set forth the distinctive characteristics of 'Silver Summer'. The data which define these characteristics were collected from asexual reproductions carried out in Komen, Belgium and Mijdrecht, The Netherlands. The plant history was taken on 3-year-old, plants grown in 1.5 liter containers outdoors during the spring. The range of daytime temperature was 12° C. to 27° C. and the range of night-time temperature was from 5° C. to 15° C. No growth retardants were used. The color readings were determined under natural light. Color references are to the R.H.S. Colour Chart of The Royal Horticultural Society of London (R.H.S.) (2001).

DESCRIPTION OF THE NEW PLANT

Classification:
- *Family.*—Lamiaceae.
- *Botanical name.*—*Lavandula stoechas.*
- *Common name.*—French lavender, topped lavender.
- *Denomination.*—'Silver Summer'.

Parentage: Whole plant mutation of *Lavandula stoechas* 'Alexandra' (unpatented).

Plant:
- *Form and habit.*—Perennial subshrub.
- *Growth and branching habit.*—Broadly upright and free-branching.
- *Plant shape.*—Globular.
- *Height* (*from top of soil, including inflorescence*).—22.8 cm.
- *Width* (*spread*).—36.5 cm.
- *Vigor.*—Low to moderate.
- *Growth rate.*—Approximately 4.0 cm per month in the spring.
- *Time to produce a finished flowering plant.*—About 32 weeks.

*Outdoor plant performance.*—Use in 12.0 cm pots or larger or in flower beds.

*Fragrance.*—All parts of the plant are strongly aromatic with a fragrance typical of *Lavandula stoechas*.

*High temperature tolerance.*—At least up to 40° C.

*Low temperature tolerance.*—Hardy to at least to USDA Zone 7.

Stems:

*Branching.*—Basal; free-branching.

*Total number of lateral branches.*—124.

*Length* (*excluding inflorescence*).—7.7 cm.

*Diameter.*—0.2 cm.

*Internode length.*—1.2 cm.

*Appearance/shape.*—Quadrangular and dull.

*Strength.*—Strong.

*Color.*—RHS 194A and RHS 194B (greyed-green).

*Texture.*—Tomentose; densely covered with wooly hairs. Length of hairs: 0.02 cm. Color of hairs: RHS 193C and RHS 193D (greyed-green).

Leaves:

*Arrangement.*—Single and opposite.

*Quantity per lateral branch.*—12 (6 pairs).

*Shape.*—Linear, carinate.

*Apex.*—Acute.

*Base.*—Cuneate.

*Margin.*—Entire.

*Texture* (*both surfaces*).—Wooly tomentose and dull; length of pubescence is 0.02 cm and pubescence color is RHS 198D (greyed-green).

*Size.*—Length: 3.0 cm. Width: 0.5 cm.

*Immature leaf.*—Color: Upper surface: RHS 137B (green). Lower surface: RHS 137C (green).

*Mature leaf.*—Color: Upper surface: RHS 189A (greyed-green). Lower surface: RHS 191A (greyed-green).

*Venation.*—Pinnate.

*Vein color.*—Upper surface: RHS 194B (greyed-green). Lower surface: RHS 191B (greyed-green).

*Petioles.*—Absent, leaves are sessile.

*Durability of foliage to stresses.*—High.

Inflorescence buds:

*Shape.*—Ovate.

*Length.*—0.4 cm.

*Diameter.*—0.2 cm.

*Rate of opening.*—Approximately 5 days

*Color.*—RHS 194B (greyed-green).

Inflorescence:

*Type and form.*—Spike and single.

*Arrangement.*—Terminal spike.

*Inflorescence size.*—Height: 4.2 cm (excluding peduncle). Width: 1.4 cm but the sterile bracts on top of the spikes have an average spread of 2.7 cm.

*Quantity of flowers per inflorescence.*—69.

*Quantity of buds per stem.*—69.

*Quantity of open inflorescences and buds per plant.*—2500.

*Blooming habit.*—Blooms once per year, continuously, during the spring to later summer.

*Rate of inflorescence opening.*—Approximately 30% of the flowers are open at any given time.

*Lastingness of the inflorescences on the plant.*—About 8 weeks.

Flower:

*Aspect.*—Outward.

*Type and appearance.*—Self-cleaning; individual flowers are sessile (no pedicels).

*Shape.*—Salverform, with one upper petal (split into two identical lobes) and one lower petal (split into three lobes, identical to upper lip).

*Size.*—Depth (height): 1.2 cm. Diameter: 0.35 cm.

*Flower longevity on the plant.*—About 10 days.

Petals:

*Arrangement.*—Rotate.

*Quantity.*—2.

*Shape.*—Spathulate with the lower 85% of each petal fused into a tube.

*Apex.*—Rounded.

*Base.*—Fused.

*Margin.*—Entire.

*Texture.*—Dull and smooth.

*Size.*—Length: 1.2 cm. Width: Upper lip petals are 0.25 cm and lower lip petals are 0.35 cm.

*Color when opening and fully opened* (*both surfaces*).—RHS N92B (violet-blue) and RHS N92C (violet-blue) but darker; the tube is RHS N155A (white).

*Color, fading to.*—RHS N92B (violet-blue) but darker.

*Texture* (*both surfaces*).—Smooth, slightly glossy.

*Peduncle.*—Length: 5.3 cm. Diameter: 0.2 cm. Angle: 0 degrees; peduncle is straight and upright. Strength: Strong. Color: RHS 194A and RHS 194B (greyed-green) but densely covered with a wooly pubescence which is RHS 193C and RHS 193D (greyed-green).

Calyx:

*Shape.*—Campanulate tube.

*Length.*—0.35 cm.

*Diameter.*—0.2 cm.

*Sepals.*—Quantity: 5. Arrangement and shape: Linear and fused into a campanulate tube. Appearance and texture: Dull, densely woolly tomentose; pubescence is less than 0.02 cm long and is RHS 190C and RHS 190D (greyed-green). Apex: Acute. Base: Fused. Margin: Entire. Size: Length: 0.35 cm. Width: 0.1 cm. Color (both immature and mature and both surfaces): RHS 144B and RHS 144C (yellow-green) but the base is lighter, RHS 145C.

Bracts:

*Fertile.*—Location: At the base of each individual flower. Shape: Broad rhomboidal. Quantity per inflorescence: 1. Margin: Entire. Apex: Rounded and 3-lobed. Base: Cuneate. Texture (both surfaces): Dull, densely woolly and tomentose; pubescence is about 0.02 cm long and RHS 193D (greyed-green). Length: 0.7 cm. Width: 0.6 cm. Color (both surfaces): RHS 194C and RHS 194D with darker RHS N189A and RHS 189B veins.

*Sterile.*—Location: On top of each spike. Quantity per inflorescence: 4. Shape: Narrow obovate. Margin: Wavy. Apex: Broad acute. Base: Cuneate. Texture (both surfaces): Dull and smooth. Length: 1.9 cm. Width: 0.8 cm. Color (both surfaces): RHS 79D (purple) but slightly lighter with an RHS 137A (green) main vein.

Reproductive organs:

*Stamens.*—Number: 4. Filament length: 0.0. Filament color: RHS. Anther shape: Dorsifixed, kidney-shaped; filament implanted in the petal. Anther length: 0.05 cm. Anther color: RHS 165B (greyed-orange). Pollen color: Close to RHS 164A and RHS 164B (greyed-orange). Pollen amount: Sparse.

*Pistil.*—Quantity: 1. Pistil length: 0.35 cm. Stigma color: RHS N186A (greyed-purple). Stigma shape: Club-shaped. Style color: RHS 155C (white). Style length: 0.3 cm. Ovary color: RHS 145C and RHS 145D (yellow-green).

Fruit and seed set: No seed set observed.

Disease and insect resistance: Average/typical of the species; no special observations made.

COMPARISON WITH PARENTAL AND COMMERCIAL CULTIVARS

'Silver Summer' differs from the parent 'Alexandra' (unpatented) in that 'Silver Summer' has leaves with a stronger intensity of grey and a lower intensity of green than 'Alexandra'.

'Silver Summer' differs from the commercial cultivar 'Avenue' (unpatented) in that 'Silver Summer' has a plant height of about 20 cm to 30 cm, while 'Avenue' has a plant height of about 30 cm to 40 cm. Additionally, 'Silver Summer' has leaves that have a stronger intensity of grey and a lower intensity of green than 'Avenue'.

I claim:

1. A new and distinct cultivar of *Lavandula* plant as shown and described herein.

* * * * *